(12) United States Patent
Korman et al.

(10) Patent No.: US 8,537,365 B1
(45) Date of Patent: Sep. 17, 2013

(54) MASS GAUGING DEMONSTRATOR FOR ANY GRAVITATIONAL CONDITIONS

(75) Inventors: Valentin Korman, Huntsville, AL (US); Kevin W. Pedersen, Huntsville, AL (US); William K. Witherow, Huntsville, AL (US)

(73) Assignee: The United States of America as represented by the Administrator of the National Aeronautics and Space Administration, Washington, DC (US)

( * ) Notice: Subject to any disclaimer, the term of this patent is extended or adjusted under 35 U.S.C. 154(b) by 372 days.

(21) Appl. No.: 12/874,946

(22) Filed: Sep. 2, 2010

(51) Int. Cl.
*G01B 9/02* (2006.01)
(52) U.S. Cl.
USPC .......................................... 356/450
(58) Field of Classification Search
USPC .......................... 356/450, 451, 517
See application file for complete search history.

(56) References Cited

U.S. PATENT DOCUMENTS

| 4,665,747 | A | 5/1987 | Muscatell |
| 5,798,834 | A | 8/1998 | Brooker |
| 6,064,630 | A | 5/2000 | Fersht et al. |
| 6,389,044 | B1 | 5/2002 | Smith |
| 6,842,256 | B2 | 1/2005 | Hill |
| 7,042,574 | B2 | 5/2006 | Hill |
| 7,330,262 | B2 * | 2/2008 | Siepmann et al. ............ 356/441 |
| 7,489,407 | B2 | 2/2009 | Hill et al. |
| 2002/0048026 | A1 | 4/2002 | Isshiki et al. |
| 2006/0288758 | A1 * | 12/2006 | Woo et al. ...................... 73/1.58 |
| 2010/0195110 | A1 * | 8/2010 | Iwai et al. ..................... 356/450 |

OTHER PUBLICATIONS

Yallin, Azer et al. "RocketSat Conceptual Design Review". Colorado State University, Nov. 6, 2009.*
Sullenberger, Ryan M. et al. "Fiber-Optic Mass Gauging System for Measuring Liquid Levels in a Reduced Gravity Environment". 46th AIA/ASME/SAE/ASEE Joint Propulsion Conference & Exhibit, Jul. 25-28, 2010, pp. 1-10.*

* cited by examiner

*Primary Examiner* — Michael A Lyons
(74) *Attorney, Agent, or Firm* — Absolute Technology Law Group, LLC; James J. McGroary

(57) ABSTRACT

The present invention is a mass gauging interferometry system used to determine the volume contained within a tank. By using an optical interferometric technique to determine gas density and/or pressure a much smaller compression volume or higher fidelity measurement is possible. The mass gauging interferometer system is comprised of an optical source, a component that splits the optical source into a plurality of beams, a component that recombines the split beams, an optical cell operatively coupled to a tank, a detector for detecting fringes, and a means for compression. A portion of the beam travels through the optical cell operatively coupled to the tank, while the other beam(s) is a reference.

21 Claims, 4 Drawing Sheets

MASS GAUGING DEMONSTRATOR FOR ANY GRAVITATIONAL CONDITIONS

FEDERAL RESEARCH STATEMENT

The invention described herein was made in the performance of work under a NASA contract and by an employee of the United States Government and is subject to the provisions of Public Law 96-517 (35 U.S.C. §202) and may be manufactured and used by or for the Government for governmental purposes without the payment of any royalties thereon or therefore. In accordance with 35 U.S.C. §202, the contractor elected not to retain title.

TECHNICAL DESCRIPTION OF THE INVENTION

The present invention relates to the field of mass gauging and more specifically to an optical interferometric method to measure the number of gas molecules supporting a compression mass gauging system.

BACKGROUND OF THE INVENTION

The ability to accurately measure quantities of cryogenic fluids in a low gravity environment is a critical requirement for future space exploration missions. In low gravity, the position of the liquid in the container may be markedly different than it is in a one-g gravity field environment. Instead of settling in the bottom of the container, the fluid may become a mixture of gas bubbles interspersed within the liquid, which may be located randomly throughout the container. As a result, the familiar gauging methods used on earth are generally not applicable in space.

Many low-g quantity gauges have been investigated in concept or by laboratory testing. These systems have been based on the use of a variety of physical principles, such as radio frequency microwaves, gas bubble resonant frequency, liquid heat capacity, optical absorbency, ultrasonics, acoustics, gamma ray densitometry, and flow meters for monitoring liquids leaving and entering a tank (mass balancing). All these techniques, however, have proved to have significant limitations in gauging accuracy, complexity, or weight.

Future space mission concepts are severely limited by the inability to determine the amount of a fluid (especially a cryogen) in a tank without some form of stratification (gravity, thermal, etc.). The nature of the fluid in a low-gravity or zero-gravity environment makes metering concepts difficult. The physics governing the flow of liquids under these conditions is dominated by surface tension and viscosity forces.

Various mass gauging schemes have been proposed and/or tried. Some require complex modifications or inside surface polishing of tanks. Others rely on complex pumping devices to apply a pressure change with a piston or pump, changing the pressure inside the vessel. The volume may then be derived from ideal gas (or similar) equations of state. This requires the belief that thermodynamics only applies when it is to the benefit of the measurement. For any fluid (especially a cryogenic one), as the pressure changes so do the physical conditions in the fluid, i.e., a pressure drop would drive the transition of more gas from the liquid.

Current compression or pump mass gauging schemes are not desirable because they suggest that about ⅓ of the tank volume be displaced in order to obtain the needed accuracy using pressure transducers.

The principles of interferometry are well known. Interferometers operate by measuring the difference in the optical phase of two electromagnetic waves. A source of radiation, commonly a coherent laser source, is split and sent along separate paths. When the beams are recombined, any resulting difference in optical phase between the paths will cause the formation of fringes with a separation equal to some half-integer multiple of the wavelength.

The observed interference pattern is a composition of bright and dark bands or fringes formed by constructive and destructive interference of light between the two different optical paths. Any shift in this pattern directly relates to a change in the phase between the two paths.

It is desirable to have a mass gauging system that will work in a range of gravity and acceleration conditions.

It is desirable to have a mass gauging system that is highly accurate, functions independently of liquid orientation, and which is only minimal intrusive (e.g., does not require that a large tank volume be displaced).

It is further desirable to have a smaller piston or other compression means resulting in reduced size and weight.

SUMMARY OF THE INVENTION

The present invention is a mass gauging interferometry system used to determine the volume contained within a tank. By using an optical interferometric technique to determine gas density and/or pressure a much smaller compression volume or higher fidelity measurement is possible.

The mass gauging interferometer system is comprised of an optical source, a component that splits the optical source into a plurality of beams, a component that recombines the split beams, an optical cell operatively coupled to a tank, a detector for detecting fringes, and a means for compression. A portion of the beams travels through the optical cell operatively coupled to the tank, while the other beam(s) is a reference.

The compression means is used to change the volume of gas in the system. A change in the volume results in a change in density, which causes a fringe shift. The fringe shift is measured and applied to a calibration to determine the volume in the tank.

GLOSSARY

As used herein, the term "cryogenic tank" refers to a receptacle suitable for storage of substances at low temperatures.

As used herein, the term "coupled" means joined or connected.

As used herein, the term "mirror" refers to an object having at least one reflective surface that reflects all or a portion of an emitted optical beam.

As used herein, the term "beam splitter" refers to an optical device that splits a beam of light into two or more beams.

As used herein, the term "optical fringe" refers to one of the alternate light and dark bands caused by separating an original source into two separate beams and then recombining them at differing angles of incidence on a viewing surface.

As used herein, the term "fringe shift" refers to the behavior of a pattern of fringes when the phase relationship between the component sources changes.

As used herein, the term "interference pattern" refers to the wave pattern that results from the addition of two or more waves.

As used herein, the term "index of refraction" or "refractive index" refers to a measure of the speed of light in a substance expressed as a ratio of the speed of light in a vacuum relative to the speed in the substance.

As used herein, the term "compression cycle" refers to the duration in which a temporary change in pressure within a closed system is effectuated and in which the system returns to its normal state.

DETAILED DESCRIPTION OF INVENTION

Figure 1:
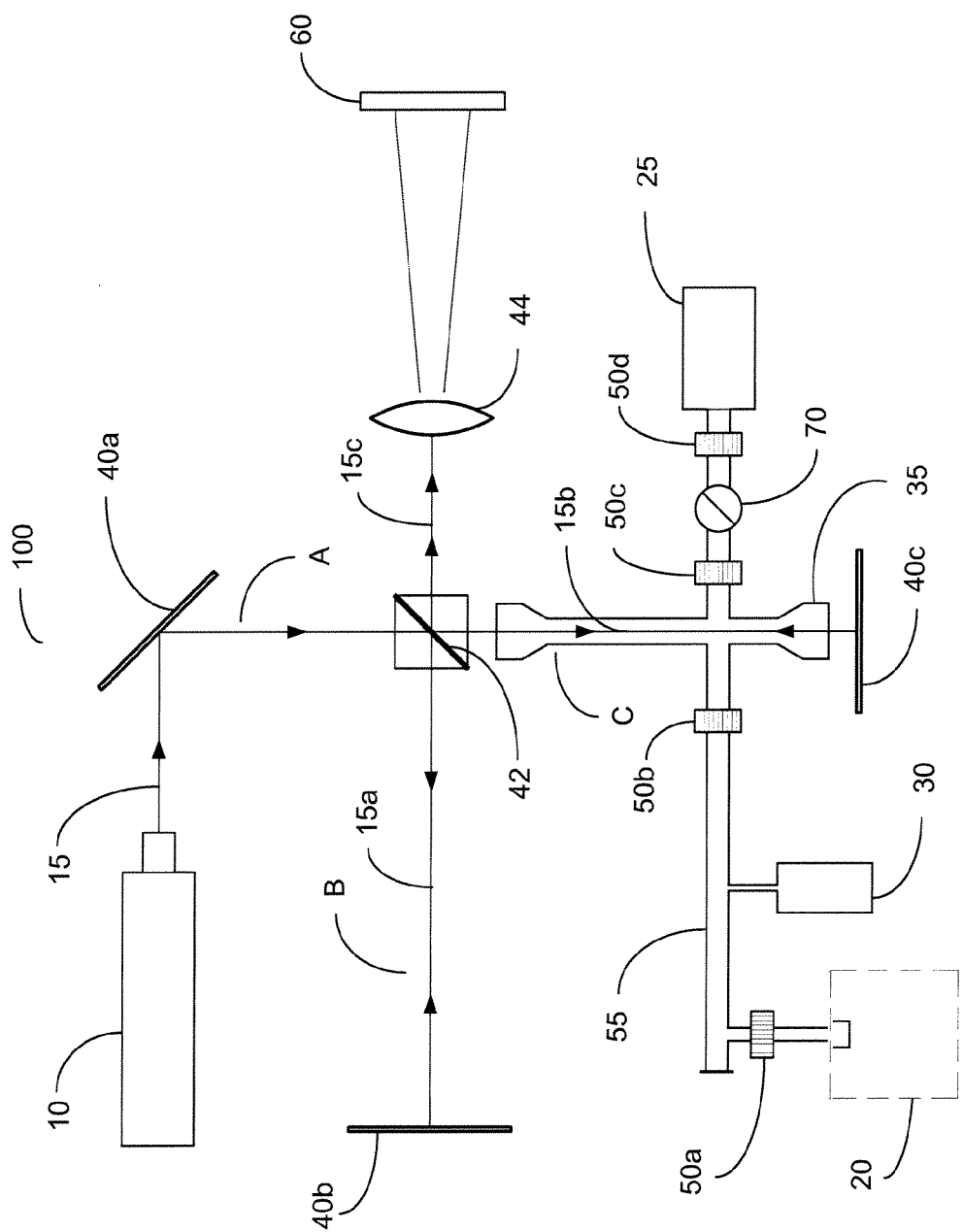
FIG. 1 illustrates a diagram of an exemplary embodiment of a mass gauging interferometer system used in a laboratory setting.

For the purpose of promoting an understanding of the present invention, references are made in the text to exemplary embodiments of a mass gauging interferometer, only some of which are described herein. It should be understood that no limitations on the scope of the invention are intended by describing these exemplary embodiments. One of ordinary skill in the art will readily appreciate that alternate but functionally equivalent components, materials, and arrangements may be used. The inclusion of additional elements may be deemed readily apparent and obvious to one of ordinary skill in the art. Specific elements disclosed herein are not to be interpreted as limiting, but rather as a basis for the claims and as a representative basis for teaching one of ordinary skill in the art to employ the present invention.

It should be understood that the drawings are not necessarily to scale; instead, emphasis has been placed upon illustrating the principles of the invention. In addition, in the embodiments depicted herein, like reference numerals in the various drawings refer to identical or near identical structural elements.

Moreover, the terms "substantially" or "approximately" as used herein may be applied to modify any quantitative representation that could permissibly vary without resulting in a change in the basic function to which it is related.

FIG. 1 illustrates a diagram of an exemplary embodiment of mass gauging interferometer system 100 used in a laboratory setting. In the embodiment shown, mass gauging interferometer system 100 utilizes a modified Michelson interferometer; however, in other embodiments, mass gauging interferometer system 100 may utilize any type of interferometer known in the art (e.g., Sagnac, Rayleigh, Fabry-Pérot, and Fourier-transform).

In the embodiment shown, laser 10 is positioned so that laser beam 15 hits first mirror 40a at a 45 degree angle and is reflected. First mirror 40a changes the direction of laser beam 15 and directs it into beam splitter 42 (Path A). In the embodiment shown, first mirror 40a is optional and is used for reduce the amount of space required. In other embodiments, first mirror 40a is omitted and laser is aimed directly at beam splitter 42.

In the embodiment shown, beam splitter 42 splits laser beam 15 into two identical beams 15a and 15b by partial reflection and transmission. In the embodiment shown, beam 15a bounces off of second mirror 40b and back toward beam splitter 42 (Path B), and beam 15b passes through optical cell 35, bounces off of third mirror 40c, and passes back through optical cell 35 toward beam splitter 42 (Path C). Beams 15a and 15b recombine at beam splitter 42 to produce an interference pattern.

In various other embodiments, beam splitter 42 splits beam 15 into more than two equal or unequal beams. At least one beam must past through optical cell 35 (coupled to tank 20) while the other beam(s) are used as a reference.

In the embodiment shown, recombined beam 15c passes through lens 44 and onto screen 60. Lens 44 and screen 60 are used to magnify the resulting fringes. In other embodiments, an optional video camera 65 is focused on screen 60 and captures the generated optical fringes. In other embodiments, lens 44 is replaced with a photodetector.

In the embodiment shown, tank 20 (e.g., a cryogenic tank) is coupled to optical cell 35 via tubing 55. In other embodiments, tank 20 may be coupled to optical cell via another means that results in a closed system.

When beam 15b passes through optical cell 35, beam 15b is coupled to the physical state of the gas in tank 20. As the substance in tank 20 expands (or contracts), the gas in the optical cell 35 changes in density resulting in a change in the index of refraction.

In the embodiment shown, beam splitter 42 is a half-silvered mirror comprised of a plate of glass with a thin coating of aluminum. The aluminum coating is of a thickness that when light hits the surface at a 45 degree angle, half of the light is transmitted (Path C), and the remainder is reflected (Path B). In other embodiments, a coating other than aluminum is used (e.g., a dielectric optical coating). In various other embodiments, a partially reflective mirror or a refractive lens is used to split and recombine the various beams.

In the embodiment shown, mirrors 40a, 40b, and 40c are fixed. The placement of mirrors and the types of mirrors may vary depending on the type of interferometer used. In various other embodiments, an optical source other than a laser is used.

In the embodiment shown, mass gauging interferometer system 100 further includes joints 50a, 50b, 50c, and 50d which are used to assemble tubing 55.

The phase difference between beams 15a and 15b may be the result of a change in path length or a change in the refractive index along the path. Using an interferometer to measure the density change in the gas rather than a standard pressure transducer increases the sensitivity of the mass gauging system. As the volume in tank 20 changes the pressure of the gas or vapor will also change.

The resulting fringe shift for a double pass interferometer (i.e., where the mirrors are fixed and only the optical path is altered through a change in the index of refraction) is calculated by Equation 1:

$$\Delta m = \frac{Ad}{\lambda} \Delta n.$$

In equation 1, $\Delta m$ is the amount (whole and fractional) of the fringe shift, measured in number of unit fringes which move past a viewing point, A is a constant depending on the type of interferometer employed and represents the number of times the beam is split, d is the length of each path of the interferometer, $\lambda$ is the wavelength of the light, and $\Delta n$ is the change in index of the gas in one of the paths. For example, when $\Delta m=1$, one bright fringe has moved exactly to the next bright fringe's previous location.

Any change in the density of a gas in tank 20 yields a change in the index of refraction where the fringe shift observed corresponds to Equation 1. The density of the gas in optical cell 35, i.e., Path 3, is determined from a measurement of the index of refraction. As the sample in tank 20 expands (or contracts), the gas in tank 20 changes in density, and as a result the index of refraction of beam 15b changes. Piston chamber 30 is used to remove system errors inherent to the gas dynamics. The motion of piston chamber 30 will yield a certain fringe shift when the sample is in one physical state, and a different fringe shift will result from the piston's motion when the sample in tank 20 is in another physical state (e.g., solid and liquid).

Piston chamber 30 must be highly repeatable and accurate to achieve proper results. Error sources to the fringe motion may be ignored so long as they can be assumed constant over the timescale of a cycle of piston chamber 30. In various embodiments, a compression means other than a piston chamber may be used.

The difference in the fringe shifts relates to the volume change of the sample. To calibrate for a specific tank, tank 20 is emptied (in an environment where gravity is present), piston chamber 30 is moved, and the number of fringes during a compression cycle is measured. Tank 20 is then filled so that it is half full. Piston chamber 30 is moved and the number of fringes measured. The process is repeated with a full tank. These three data points can be used to determine a calibration, which is later used to determine the volume in a tank with an unknown volume.

For a gas, pressure is related to gas density which can be measured as the optical refractive index. Various models may be used to explain the relationship between gas density and index of refraction, i.e., how gases behave optically. For example, the Lorentz-Lorenz relation, Equation 2, relates the microscopic properties of a particular gas species to the macroscopic properties of the entire ensemble:

$$\propto (v) = \frac{3}{4\pi N}\left[\frac{n(v)^2 - 1}{n(v)^2 + 2}\right].$$

Here $\propto$ is the electric dipole polarizability and depends on the frequency (v) of the incident electromagnetic radiation and on the atomic species. N is the number density within the gas and n is the index of refraction of the gas, also a function of frequency. It is valid for gases of ground state atoms or nonpolar molecules at optical wavelengths.

Another example, the Gladstone-Dale relation is used for optical analysis. The Gladstone-Dale relation linearly relates the index of refraction to glass density; however, is not as precise as the Lorentz-Lorenz relation.

The Clausius-Mossotti relation is another example used to analyze the relationship between the dielectric constants and it typically for radio and microwave wavelengths, not visible light.

The volume of the system can be determined by the Equation 3:

$$V_s = \frac{\Delta m_1}{\beta_{1,2}\Delta m_2 - \Delta m_1}V_c - V_p.$$

In Equation 3, $V_s$ is the system volume and includes all the volume the gas occupies in tank 20, tubing 55, and optical cell 35. The value of $V_s$ is initially estimated and subsequently experimentally determined. $V_c$ is the fixed volume of control volume which is connected to tubing 55 via binary shut-off valve 70. The pressure, gas number density in $V_c$ is the same as the initial fill pressure in $V_s$. $V_p$ is the volume of precisely control piston chamber 30.

Piston chamber 30 is always connected to the mass gauging interferometer system 100 and is changed by a precision drive system (not shown). Piston chamber is pulled down or pushed up to increase and decrease the total volume. This increases decreases and increases, respectively, the gas number density and causes apparent motion in the fringes. The resulting fringe count data can be extracted and used to determine the system volume $V_s$.

Interferometers can easily obtain accuracy on the magnitude of $10^{-6}$, which is at least $10^4$ times better than a mass gauging system that utilizes a pressure transducer. In addition, the use of an interferometer requires the use of a much smaller and lighter compression system (approximately 1000 times smaller) than other mass gauging systems.

In addition, mass gauging interferometer system 100 allows the volume in a tank to be determined in varying gravity and acceleration conditions. Unlike other mass gauging systems, mass gauging interferometer system 100 does not require that the volume be settled in one portion of the tank and can be used to measure the volume in a tank containing sloshing liquid or liquid containing gas bubbles. Mass gauging interferometer system 100 may be used to determine the volume of a cryogenic fluid, a liquid propellant, liquid hydrogen, a hazardous substance, or any or substance contained within a closed system.

Figure 2:
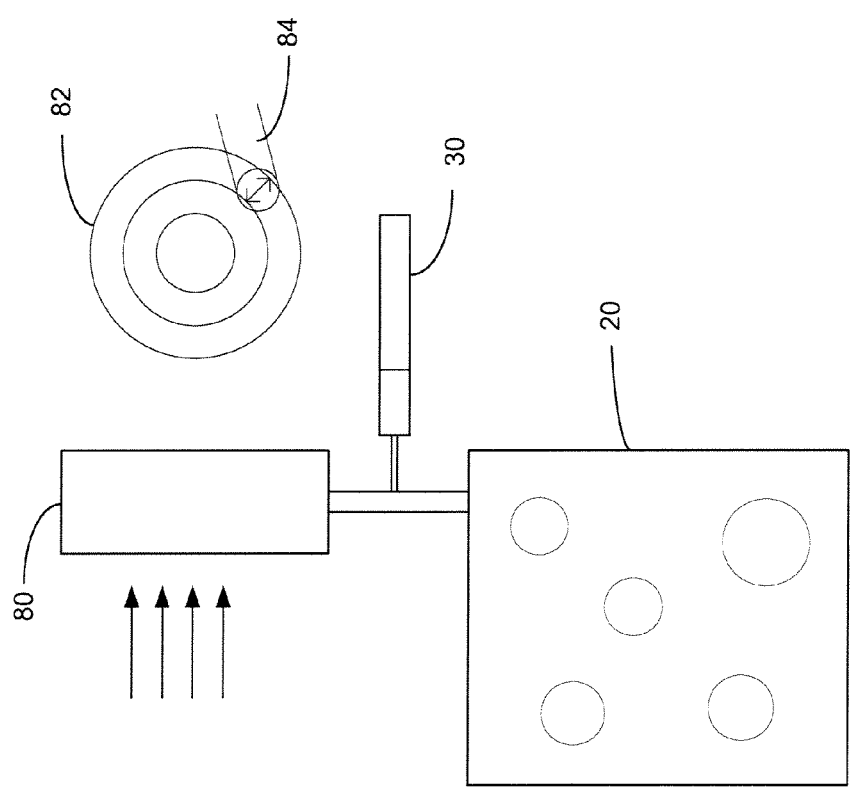
FIG. 2 illustrates an exemplary embodiment of a mass gauging interferometer system.

FIG. 2 illustrates an exemplary embodiment of mass gauging interferometer system 100. Visible in FIG. 2 are tank 20, piston chamber 30, interferometer 80, optional detector 82, and detector 84. In the embodiment shown, optional detector 82 is a spectrometer which may be used in applications where more than one type of gas is present. For example, in applications where the system contains both helium and oxygen, the spectrometer may be used to determine how much of each gas is present.

In the embodiment shown, detector 84 is a fringe counter (e.g., a photodiode) used to measure the index of refraction of the gas via a fringe count. The fringe counter counts the number of fringes that moved past a viewing point. The fringe shift is applied to a calibration for the specific tank to determine the volume. In order to determine the index of refraction.

In the embodiment shown, interferometer 80 contains an optical or gas cell and may be any type of interferometer known in the art.

In various embodiments, mass gauging interferometer system 100 further includes a graphical user interface that displays the volume (i.e., the amount of liquid) in tank 20. For example, mass gauging interferometer system 100 may include a fuel gauge.

Figure 3:
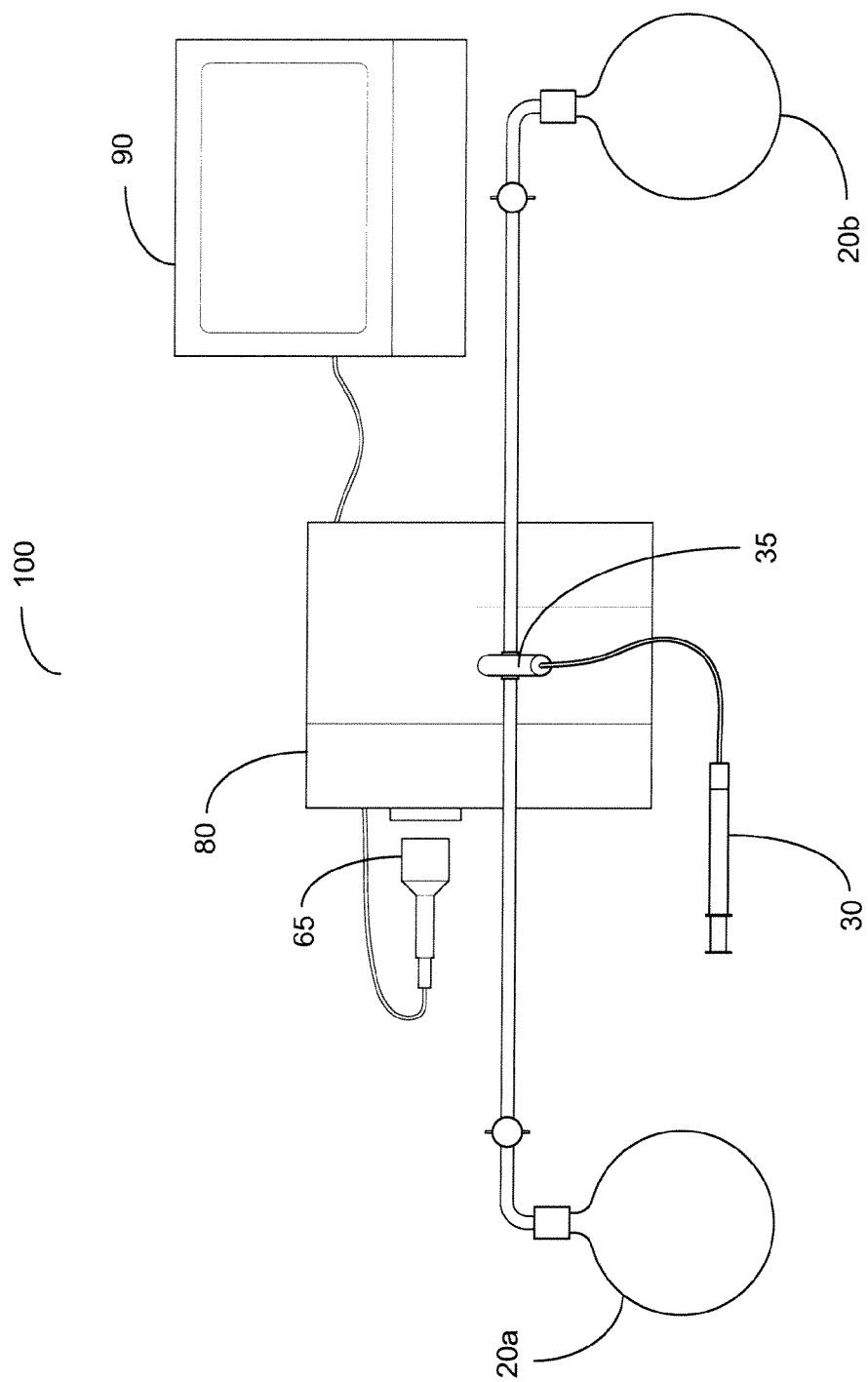
FIG. 3 illustrates an elevated front view of an exemplary embodiment of a mass gauging interferometer system used in a laboratory setting.

FIG. 3 illustrates an elevated front view of an exemplary embodiment of mass gauging interferometer system 100 used in a laboratory setting. Visible in the embodiment shown are tanks 20a and 20b, piston chamber 30, control volume 25, tubing 55, optical cell 35, interferometer 80, video camera 65, and video monitor 90.

In the embodiment shown, tanks 20a and 20b each contain a different volume. For example, tank 20a may be full and tank 20b may be half full.

In the embodiment shown, interferometer 80 contains all of the optics and may be any type of interferometer known in the art.

Figure 4:
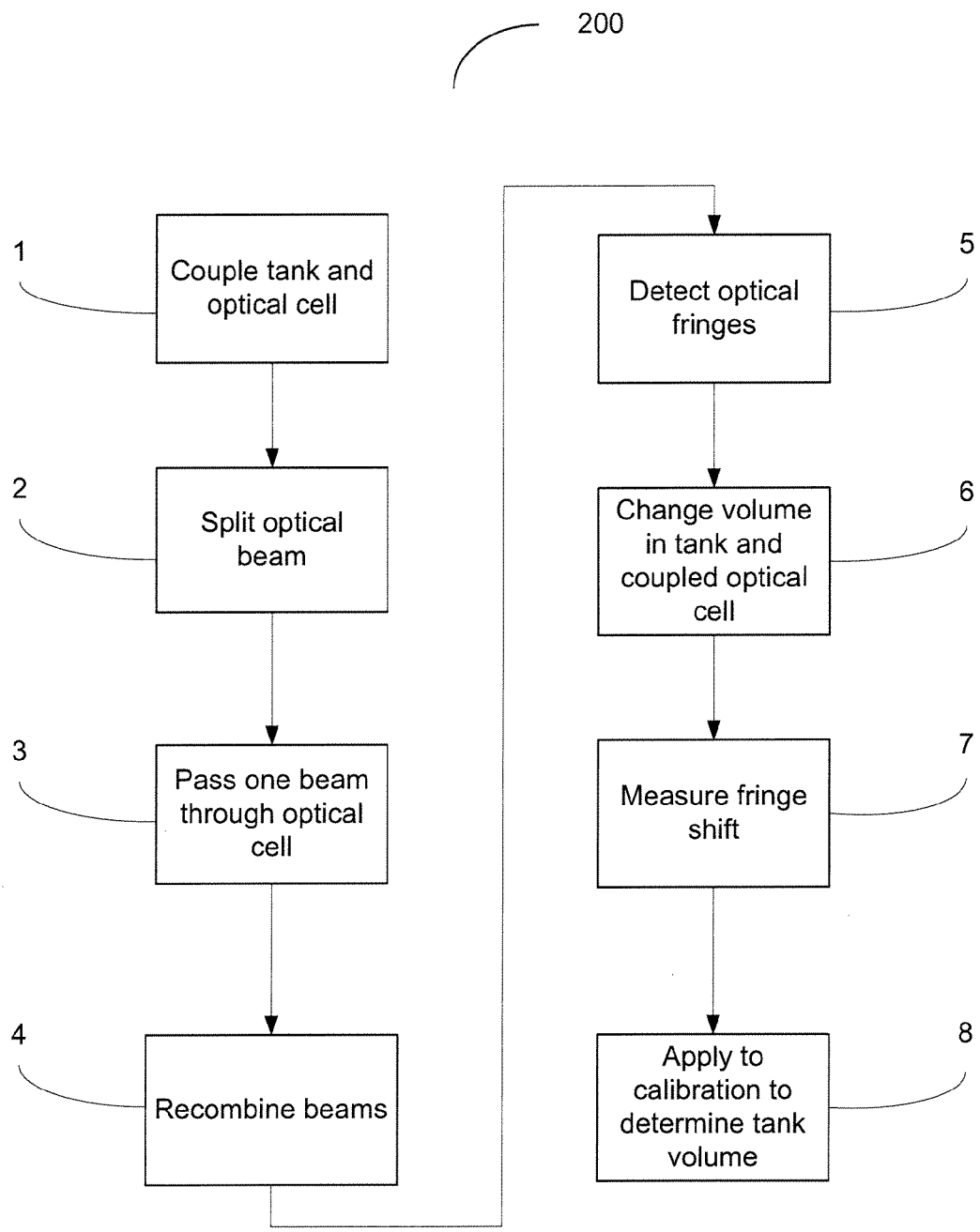
FIG. 4 illustrates an exemplary method of calculating the volume in a system using a mass gauging interferometer system.

FIG. 4 illustrates method of calculating the volume in a system 200 using mass gauging interferometer system 100. In Step 1, a tank with an unknown volume is coupled to an optical cell. In Step 2, the beam is split into multiple beams. In various embodiments, the beam may be split using a beam splitter, partially reflective mirror, or a lens. In Step 3, one of the beams is passed through the optical cell.

In Step 4, the beams are recombined. In Step 5, the optical fringes are detected. In Step 6, the volume in the tank and coupled optical cell is changed (e.g., using a piston or bladder). The change in density causes a shift in the optical fringes and in Step 7, the fringe shift is measured. In Step 8, calibration is applied to determine tank volume.

In various other embodiments, the recombined beam may be passed through a lens and depicted on a screen in order to magnify the fringes.

What is claimed is:

1. A compression mass gauging interferometer system comprised of:
    a tank operatively coupled to an optical cell;
    an optical source;
    a component to split said optical source into a plurality of beams;
    wherein at least one of said plurality of beams passes through said optical cell;
    a component to recombine said multiple beams;
    a detector for detecting fringes; and
    a means for compression.

2. The system of claim 1 wherein said optical source is a laser.

3. The system of claim 1 which further includes at least one reflective surface.

4. The system of claim 1 which further includes at least one refractive surface.

5. The system of claim 1 wherein said component to split said optical source and said component to combine said multiple beams are selected from a group consisting of a beam splitter, a partially reflective mirror, and a lens.

6. The system of claim 1 wherein said means for compression is a piston.

7. The system of claim 1 which further includes a means for detecting and counting number of said fringes that pass a fixed point during a compression cycle.

8. The system of claim 1 wherein changing the gas density in said system changes the index of refraction and number of said fringes.

9. The system of claim 1 which further includes a means for correlating a change in number of said fringes to a volumetric change within said system.

10. The system of claim 1 which further includes a graphical user interface which displays the amount liquid in said tank.

11. They system of claim 10 wherein said graphical user interface is a fuel gauge.

12. The system of claim 1 wherein said tank is a cryogenic tank.

13. The system of claim 1 wherein said tank holds a substance selected from a group consisting of a cryogenic fluid, a liquid propellant, liquid hydrogen, and a hazardous substance.

14. The system of claim 1 which further includes a plurality of reflective mirrors.

15. The system of claim 1 which further includes a lens mechanically adapted to operate in pressure, temperature, and gas environment of said tank.

16. The system of claim 1 wherein said interferometer is a modified Michelson interferometer.

17. The system of claim 1 which further includes a control volume.

18. The system of claim 1 which further includes a binary shut-off valve.

19. A method of measuring the volume in a tank comprised of the steps of:
    coupling a tank with an unknown volume to an optical cell;
    splitting a beam into multiple beams;
    passing at least one beam through said optical cell;
    recombining said multiple beams;
    detecting optical fringes;
    changing volume in said tank and coupled optical cell;
    measuring fringe shift; and
    applying calibration to determine volume in said tank.

20. The method of claim 19 which further includes the step of magnifying and displaying said optical fringes on a screen.

21. The method of claim 19 which further includes the step of calibrating to determine number of optical fringes which correlate to tank volume.

* * * * *